United States Patent [19]

Liu

[11] Patent Number: 5,444,807
[45] Date of Patent: Aug. 22, 1995

[54] MICRO CHEMICAL ANALYSIS EMPLOYING FLOW THROUGH DETECTORS

[75] Inventor: Su Y. Liu, Sarasota, Fla.

[73] Assignee: World Precision Instruments, Inc., Sarasota, Fla.

[21] Appl. No.: 242,739

[22] Filed: May 13, 1994

Related U.S. Application Data

[63] Continuation-in-part of Ser. No. 169,310, Dec. 17, 1993, which is a continuation-in-part of Ser. No. 38,520, Mar. 29, 1993, abandoned.

[51] Int. Cl.⁶ .............................. G02B 6/20
[52] U.S. Cl. .................... 385/125; 385/12; 385/13; 250/227.25
[58] Field of Search ............ 385/125, 12, 13, 123, 385/143; 250/227.25, 227.19

[56] References Cited

U.S. PATENT DOCUMENTS

| | | | |
|---|---|---|---|
| 3,894,788 | 7/1975 | Gambling et al. | 385/125 |
| 3,995,934 | 12/1976 | Nath | 385/125 |
| 4,045,119 | 7/1977 | Eastgate | 385/125 |
| 5,030,010 | 7/1991 | Birkle | 385/125 X |
| 5,165,773 | 11/1992 | Nath | 385/125 |
| 5,304,171 | 4/1994 | Gregory et al. | 385/125 X |

FOREIGN PATENT DOCUMENTS

| | | | |
|---|---|---|---|
| 2719504 | 11/1978 | Germany | 385/125 |
| 57-30802 | 2/1982 | Japan | 385/125 |

OTHER PUBLICATIONS

"Ultra-Sensitive UV Detection in Micro Separation", Journal of High Resolution Chromotography, 1989, J. P. Chervet et al, pp. 278-281.

"Micropipette Adaptor for Spectrophotometers", Rev. Sci. Instrum. 61 (5), May 1990, H. R. Garner et al, pp. 1433-1435.

*Primary Examiner*—Rodney B. Bovernick
*Assistant Examiner*—Hemang Sanghavi
*Attorney, Agent, or Firm*—Chilton, Alix & Van Kirk

[57] ABSTRACT

The chemical properties of a flowing liquid analyte, the analyte comprising a solvent having an index of refraction which is the same as or closely approaches that of water, are determined by liquid chromatography or capillary electrophoreses wherein the analyte is caused to flow through an optical waveguide. The waveguide is a rigid capillary having a refrctive index of less than 1.33. Measurement light is launched axially into the analyte by inserting an optical fiber, coupled to a light source, into one end of the waveguide.

21 Claims, 3 Drawing Sheets

MICRO CHEMICAL ANALYSIS EMPLOYING FLOW THROUGH DETECTORS

CROSS-REFERENCE TO RELATED APPLICATIONS

This application is a continuation-in-part of application Ser. No. 169,310 filed Dec. 17, 1993. Application Ser. No. 169,310, in turn, is a continuation-in-part of application Ser. No. 038,520 filed Mar. 29, 1993 and now abandoned.

BACKGROUND OF THE INVENTION

1. Field of the Invention

The present invention relates to the detection of analytes present in a solvent stream and particularly to the performance of light absorption and fluorescence measurements to determine the chemical properties of small amounts of fluid analyte. More specifically, this invention is directed to analytical cells which are configured as flow-through detectors and especially to microchemical analysis instruments which employ a rigid aqueous liquid core waveguide as a flow cell through which a fluid analyte is directed while being illuminated whereby light absorption by the analyte or fluorescence induced in the analyte may be measured. Accordingly, the general objects of the present invention are to provide novel and improved methods and apparatus of such character.

2. Description of the Prior Art

Ultraviolet (UV) and visible (Vis) light spectrometers, photometers and fluorometers are widely used as detectors in the fields of liquid chromatography (LC), high performance liquid chromatography (HPLC), high performance capillary electrophoresis (HPCE) and capillary electrophoresis (EC). Liquid chromatography applications, for example, are used to separate molecular species owing to their differing flow mobility. The spectrometers associated with chromatography and electrophoresis apparatii detect analytes which result from the separation of the molecular species.

UV/Vis spectrometers have long employed flow cells to detect analytes in liquid chromatography. In the prior art flow cell technology, axial illumination, i.e., illumination along the flow path of the analyte, has been commonly employed. Analytical instrument manufacturers have, for many years, unsuccessfully attempted to overcome two major deficiencies inherent in previously available flow-through spectrometers. A first deficiency relates to increasing utility by reducing analysis cell volume whereby only a small amount of sample fluid is required. The second, and somewhat contradictory problem, has been to increase instrument sensitivity by increasing the light path length to thereby maximize light interaction with the sample fluid. Employing the prior art materials and techniques, it has proven to be exceedingly difficult to increase the light path length without also significantly increasing the volume of the analysis cell. It has also proven very difficult to collimate light into a beam which is sufficiently fine so that the light can travel a long distance through the sample analyte. A long light path-length has, in fact, required resort to the use of a single wavelength collimated source such as a laser. The situation where only a single wavelength light will suffice for all of the measurements required on a given sample is highly unusual. Further, it is difficult and expensive to fabricate a flat window through which light can be externally introduced into a small flow-through analysis cell. In practice, the available light introduction windows have had the result of dispersing, i.e., defocusing, the incident light beam.

To briefly summarize the above, a common application for flow-through cells is the analysis of fluids emerging from chromatographic apparatus wherein analytes have been spatially separated owing to differences in the mobility of molecular species in fluid media. As another application, small volumes of a test analyte are injected into a carrier fluid, usually water, and the carrier fluid is then passed through a flow-through detector cell for analysis by light absorption or induced fluorescent measurements. The sensitivity of prior art optical flow-through detector cells is limited by the ability to ensure that the light path through the analyte is sufficiently long to allow the incident light to interact as fully as possible with the fluid sample. In the prior art this has necessarily implied that the sample volume required should be large and, in many cases, large volume samples are not obtainable. Further, even when a large volume sample is available, and thus a cell having an acceptably long light path length could be constructed, there were significant losses associated with introduction of the analysis light into the cell and the use of non-coherent light was thus generally considered impossible.

A number of techniques for solving the above-discussed long-standing problems have been proposed and in some cases implemented. For example, as shown in published European Patent Application No. 891067001, a flow cell with a light path length of 20 mm could theoretically be achieved through the use of a Z-shaped capillary. This approach, however, was unsuccessful in actual practice because too much of the analysis light, focused directly on one end of the capillary, was lost. High light loss, i.e., low light throughput, limits a flow cell to measurements using a single wavelength light only. Thus, even when the light path length was significantly reduced, Z-shaped capillary flow cells have not proven successful for scanning the full spectrum in the UV and Vis light range.

It should be noted that the use of capillary tubing for a cuvette and glass optical fibers for both illumination and light collection was reported by Vurek and Bowman in 1969, see Analytical Biochemistry, Vol. 29, pgs. 238–247. Such use of glass optical fibers allows the elimination of the window through which light is coupled to the sample and received from the sample. However, mere elimination of the window did not solve the light loss problem since the light travelling through the capillary was not collimated and, accordingly, the maximum path length was limited to about 10 mm.

Efforts to improve on the technique reported by Vurek and Bowman have concentrated on increasing the effective path length of capillary cuvette cells through the use of non-aqueous liquid core waveguide technology. In order for a liquid to function as a light waveguide, the walls of the containment for such liquid, i.e., the walls of the capillary tube, must have a refractive index lower than that of the liquid. Water, the principal solvent for biochemical analytes, has a refractive index of 1.33. Until very recently, there were no materials available which could be used to fabricate a capillary with a refractive index of less than 1.33. In the above-referenced co-pending application, applicant discloses an aqueous liquid filled capillary waveguide.

To continue to discuss the prior art, faced with the inability to employ water as the liquid core of a light waveguide, a number of alternative technologies were proposed. Thus, as reported by K. Fuwa et al in Analytial Chemistry, Vol. 56, pg. 1640, 1984, organic solvents with refractive indices higher than that of the glass wall of a capillary tube were employed to achieve a "long capillary cell" (LCC). Such utilization of organic solvents was reported to achieve an increase in absorbance of about $3 \times 10^4$ times. This increase in absorbance, however, required a cell 50 meters in length. Futher, the Fuwa et al technique had very limited applicability because only a few liquid organic solvents, such as carbon disulfide and benzine, could be used. A particular disadvantage of using such solvents resides in the fact that their transmittance of UV light is very poor.

Attempts to improve the performance of instruments employing an LCC included coating the internal walls of the capillary with reflective material. Such approaches are discussed by P. Dasgupta in Analytical Chemistry, Vol. 45, page 1401, 1984 and by K. Fujiwara et al in Applied Spectroscopy, Vol. 44, pgs. 1084–1088, 1990. These "mirror" approaches did not prove to be successful since a maximum of about 92% reflection could be obtained. Accordingly, after only 100 wall bounce reflections, only 0.02% of the incident light intensity remained. Dasgupta et al reported nearly a million fold loss of light intensity in a glass capillary cell 10 mm long. Additional problems resulted from the fact that the internally coated silver, which was the favored mirror material, was not flat and would also react chemically with the organic solvents. As an alternative approach, it was suggested that the outer glass surface of an LCC be coated with aluminum to reflect light at the glass-air interface. Such a proposal is discussed by L. Wei et al in Analytical Chemistry, Vol. 55, pg. 951, 1983. As yet another possibility, reported by K. Tsunoda in Analytical Science, Vol. 4, pg. 321, 1988, the capillary glass-air interface was used as the total reflecting surface without any coating. In either case where reflection was from the outer surface of the glass capillary, it has been found that some light would pass many times through the sample, some light would travel further in glass than in the sample and some light would travel only in the glass. Accordingly, the resulting fluid light absorption was not a linear function of analyte concentration and was difficult to predict.

In recent years, it has been proposed to use a fluorocarbon material to define a capillary cell. The use of a fluorocarbon material with a refractive index in the range of 1.38 to 1.5, i.e., a refractive index greater than that of water, is discussed by K. Tusunoda et al in Applied Spectroscopy, Vol. 41, pgs. 163–165, 1990 and J. Taylor et al in the Journal of Chromatography, Vol. 550, pgs. 831–837, 1991. These prior uses of capillary cells comprised of fluorocarbon material required the addition of ethanol and ethylene glycol fluids to increase the refractive index of the sample fluid so as to cause it to be greater than that of the cell defining material.

Thus, after many years of attention by researchers, a basic problem remained, i.e., the necessity of employing organic solvents with refractive indices higher than that of the walls of the capillary cell. It must be noted that, in addition to preventing the use of water as a solvent, the employment of organic solvents results in the measuring instrument being refractive index sensitive. That it, when organic solvents are employed in a LCC utilized for light aborption measurements, the refractive index effect appears on the resulting chromatograms as baseline shifts and false peaks at points where mobile phase composition is changing rapidly. Such rapid changes in mobile phase composition may result during gradient elution and sample injection. Refractive index sensitivity is a serious problem in HPLC detection systems because many organic solvents of many different refractive indices are frequently used. An absorbance detector should not measure refractive index, but should instead measure only absorbance. In conventional prior art flow cells, the lower the refractive index of the carrier fluid, the more light that will be lost. A sudden change in the refractive index of the media in the cell will introduce a sudden change in the light intensity in the detector, giving a false absorbance signal. Many complicated methods have been used with varying degrees of success to reduce this refractive index effect.

It must also be noted that fluorescence detection faces the same problems as absorbance measurement as discussed above. In the case of florescence detection, to enhance sensitivity, the excitation path length should be long. It has been proposed to increase excitation path length through the use of Pyrex glass capillary tubing, having a refractive index of 1.474, and a high refractive index mobile phase (refractive index in the range of 1.5 to 1.6) to form a waveguide. Such a system is described in K. Fujiwara et al, Applied Spectroscopy, Vol. 6, pgs. 1032–1039, 1992. The system described in the referenced article has not proven to be a practical approach because many of the frequently used mobile phases in liquid chromotography have refractive indices lower than 1.474 and, accordingly, will not function as a light waveguide.

SUMMARY OF THE INVENTION

The present invention overcomes the above-discussed and other deficiencies and disadvantages of the prior art by providing a novel technique by which light absorption and fluorescence may be used as measures of the chemical properties of small amounts of a flowing fluid analyte, particularly in conjunction with liquid chromotograpy and capillary electrophoresis processes. The present invention also encompasses apparatus for implementing the aforesaid methods, the apparatus including a flow cell which functions as an optical waveguide. In the practice of the present invention, virtually all of the liquids commonly used in liquid chromotography, including solvents such as water and methanol which have low refractive indices, can function as the liquid core of the waveguide/flow cell.

BRIEF DESCRIPTION OF THE DRAWINGS

The present invention may be better understood, and its numerous objects and advantages will become apparent to those skilled in the art, by reference to the accompanying drawings wherein like reference numerals refer to like elements in the several figures and in which.

DESCRIPTION OF THE DISCLOSED EMBODIMENTS

Figure 1:
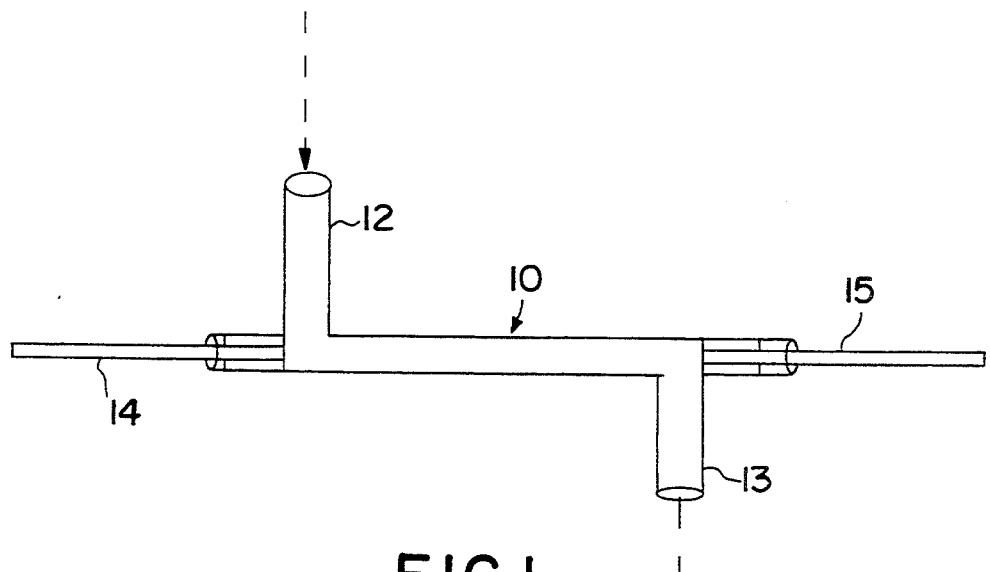
FIG. 1 is a schematic, side elevation view of a first embodiment of a flow cell for use in the practice of the present invention.

In the practice of the present invention, a rigid waveguide capillary is employed as the cell body of a flow cell for UV/Vis spectrometry, photometry and fluorometry. Such a rigid waveguide capillary is disclosed in co-pending application Ser. No. 169,310, filed Dec. 17, 1993, which is incorporated herein by reference. As described in the referenced application, the refractive index of the capillary is lower than that of either water or methanol, i.e., the refractive index of the preferred embodiment is in the range of 1.29 to 1.31. Accordingly, the capillary tube may be filled with an aqueous solution which functions as the liquid waveguide core through which light is transmitted. Restated, water, methanol and all other commonly used mobile phases (solvents) can be employed as the waveguide of a rigid liquid core waveguide capillary employed in the present invention because their refractive indices are higher than that of the cell body. The sensitivity of photometric measurement employing the invention may thus be improved in several respects. Firstly, light throughput efficiency is increased thereby acheiving a higher signal to noise ratio. Secondly, sample volume is reduced and, accordingly, less solute is needed for a given fluid concentration. Additionally, and most importantly, light path length may be increased thereby ensuring that the analyte will have enough optical density to be detectable. According to Lambert-Beers Law:

Absorbance=eCl where e is the extinction coefficient, C is the concentration of the analyte and l is the light path length. Thus, light absorption, and therefore optical density, is directly proportional to the light path length.

Theoretically, the length of a flow cell in accordance with the invention is only limited by the absorbance of the solvent and analyte. However, in actual practice, the light path length is limited by the volume of the cell. A commonly used HPLC flow cell has a volume of approximately 15 μl and a 10 mm path length. In the practice of the present invention, if a 0.3 mm inner diameter aqueous waveguide capillary is used, the path length of a cell having the same volume will be approximately 212 mm, i.e., the path length is 21 times longer than that of a conventional cell. The long light path length is especially advantageous for detecting samples with low concentration and low light absorbance, i.e., samples having a low extinction coefficient. It must be noted that the long light path length does not reduce the resolution of two closely adjacent spectral peaks because the cell volume can be significantly reduced by using smaller diameter capillary tubes.

An additional advantage incident to employing a rigid aqueous waveguide capillary as the body of a flow cell in accordance with the present invention resides in the fact that such a flow cell does not require a window at the end of the capillary. A window is not necessary, and the losses associated with dispersion of light caused by the prior art window thus eliminated, because the analysis light is launched and, in the case of an absorption measurement, collected by an optical fiber which is inserted directly into the waveguide. This increased coupling and decoupling of the light to the liquid waveguide core contributes to the ability to achieve a very long light path length when compared to prior art devices. The elimination of the window(s) at the end of the flow cell also reduces the cost of manufacture of the cell. In a conventional flow cell, a well polished window must be sealed to each end of the cell and each window must be precisely oriented so as to be perpendicular to the axis of the flow. Such fabrication is difficult and, when small dimensions are required, very expensive. In the practice of the present invention, it is simply necessary to insert two reasonably flat ended optical fibers into the opposite ends of a rigid aqueous waveguide capillary in order to enable the ability to make light absorption measurements.

FIG. 1 schematically illustrates the use of a flow through aqueous waveguide capillary 10 in a light absorption mode in accordance with the invention. As described in co-pending application Ser. No. 169,310, the cell body of the light guide 10 may be comprised of an amorphous polymer having a refractive index of less than 1.33. For example, light guide 10 may be fabricated from the fluorocarbon material available from the dupont Company under the trademark "Teflon AF 1600". Fluid to be analyzed flows into the cell at entry port 12 and leaves the cell at discharge port 13. A pressure difference between the ports 12 and 13 creates the flow. Light from an appropriate source, which may be visible, ultraviolet or infrared depending upon the analyte to be detected, is introduced into the cell and transmitted generally in the direction of the fluid flow axis via a fiber optic 14. It will be understood that, as employed here, the term "fiber optic" may mean either a single optical fiber or a bundle of fibers. Because of the waveguide properties of cell 10, as described in the co-pending application, all of the introduced light is essentially contained in the flow cell space. Attenuated light leaves the cell, after absorption by the core fluid, via a second fiber optic 15. Fiber optic 15 transmits the attenuated light to a photometric sensor such as a photodiode detector, photomultiplier or spectrophotometer.

Figure 2:
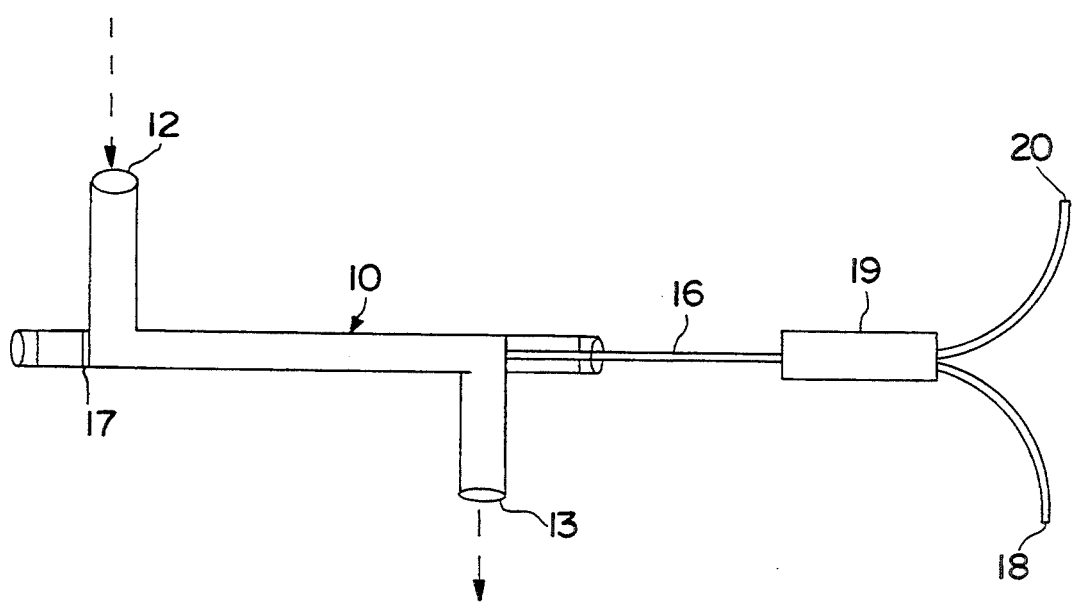
FIG. 2 is a view similar to FIG. 1 depicting a second embodiment of a flow cell for use in the practice of the invention.

In the embodiment of FIG. 2, a single fiber optic 16 is employed for both light input to and output from the flow cell. Also in the FIG. 2 embodiment, increased sensitivity is obtained by utilizing a mirror 17 at the end of the linear flow path disposed oppositely with respect to the point at which light is introduced, i.e., the mirror 7 doubles the light path length. Light from an appropriate source, not shown, is coupled to fiber optic 16 via an optic fiber 18 and a fiber optic photon coupler 19. Light received back at fiber optic 16 after having twice traversed the length of cell 10, i.e., light reflected from mirror 17, will be delivered to the photometric sensor via photon coupler 19 and a branching output fiber optic 20. It will be understood by those skilled in the art that means other than a photon coupler, for example partially reflecting mirrors, can be employed to split the incident and reflected light in the FIG. 2 embodiment.

Figure 3:
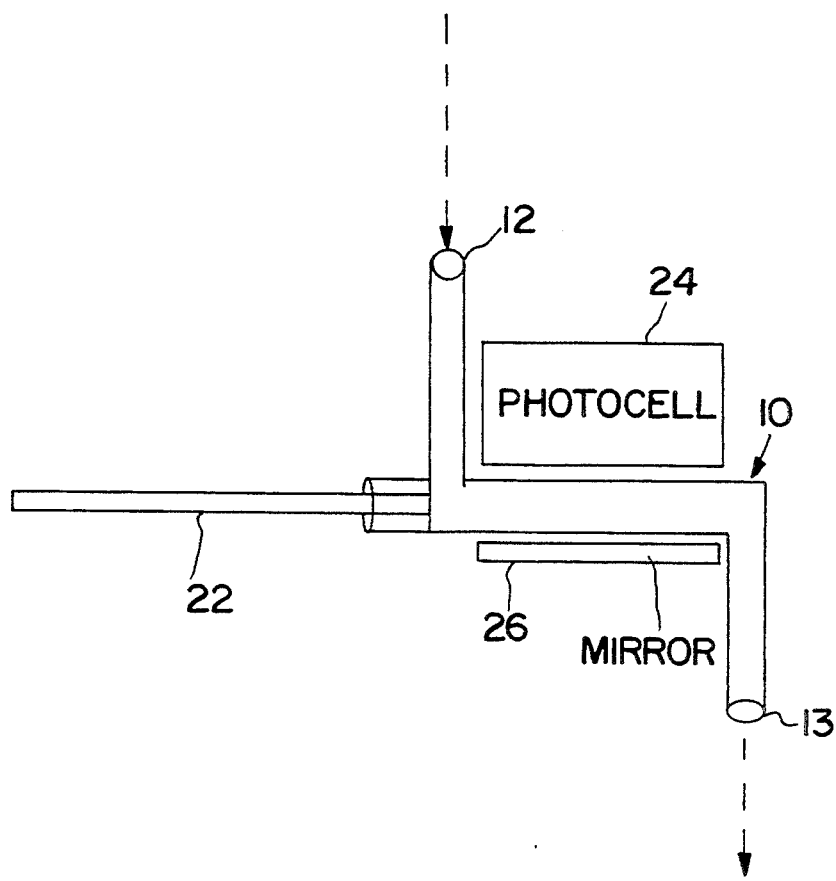
FIG. 3 is a view similar to FIGS. 1 and 2 depicting a flow cell in accordance with the present invention intended for fluorescence detection.

FIG. 3 represents a fluorescent detection apparatus in accordance with the present invention. The flow cell 10 of the FIG. 3 embodiment is substantially of the same construction as that of the absorbance cells of FIGS. 1 and 2 and thus includes an entrance port 12 and a discharge port 13. In the FIG. 3 embodiment, excitation light is introduced into the core region of the flow cell via fiber optic 22 where it excites the analyte material in the fluid stream to fluorescence. The fluorescent light emitted by the analyte is diffuse and, due to its angle on incidence on the cell wall, is not constrained in the aqueous waveguide capillary as in the absorption cell application. Accordingly, most of the fluorescent light resulting from the excitation of the analyte material will pass through the vessel wall of cell 10 in all directions. This emitted fluorescence is detected by a photo cell or photomultiplier 24 which is mounted adjacent to and in facing relationship to the aqueous waveguide capillary. Detection sensitivity may be significantly enhanced by placing a reflecting mirror 26 parallel and opposite to the detector 24, mirror 26 intercepting fluorescent light emitted in the half space below the flow-through cell and reflecting the intercepted light to the detector 24.

Figure 4A:
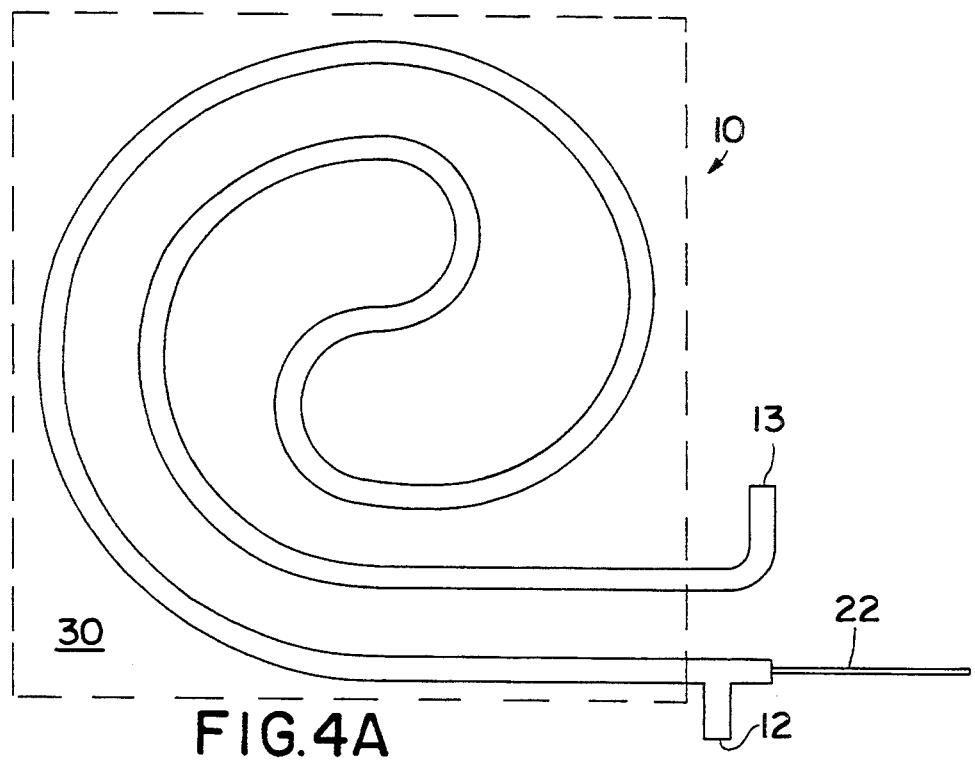
FIGS. 4A, 4B and 4C are, respectively, a schematic top plan view, a cross-sectional side elevation view and an enlarged partial view of a second alternative of a flow cell for use in fluorescence detection in accordance with the invention.
Figure 4B:
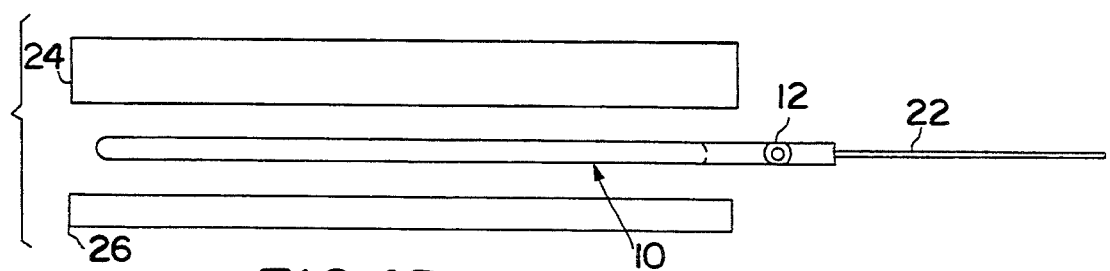
Figure 4C:
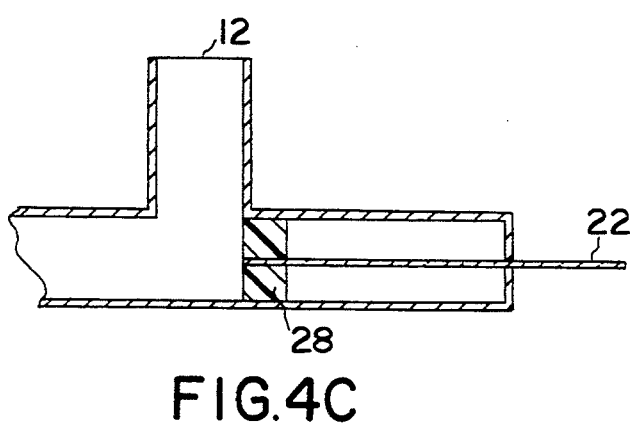

FIG. 4 depicts a fluorescent detection apparatus which is an alternative to the arrangement of FIG. 3. In the FIG. 4 embodiment, the light collection efficiency is enhanced by forming the flow-through cell into a spiral shape. Thus, as shown in FIG. 4A, a comparatively long path length between the inlet port 12 and the discharge port 13 may be compressed into a relatively small area. Excitation light is introduced into the aqueous waveguide capillary via fiber optic 22. The fiber optic insertion into the waveguide is shown in detail in the enlarged view of FIG. 4C. As may be seen in FIG. 4C, a waterproof adhesive seal 28 prevents fluid from leaking out of the flow cell and secures the fiber optic. FIG. 4B shows the physical placement between the spiral aqueous waveguide capillary 10, the detector 24 and the mirror 26. The detector and mirror are arranged in planes which are parallel to the plane defined by the axis of the flow path through cell 10 and will be generally coextensive in size with a support mechanism, schematically illustrated at 30 in FIG. 4A, for the spiraled flow cell.

In the above-described embodiments, proper design can completely eliminate the refractive index effect. For example, assuming the mobile phase of the liquid to be methanol, a NA 0.2 multimode fiber optic can be employed as the input and output light fibers for absorbance measurement and the cell may be fabricated from "Teflon AF 1600". Since the light injection and acceptance angle for an N.A. 0.22 fiber to methanol media is 9.64°, and the total reflection angle of the aqueous waveguide capillary comprised of "Teflon AF 1600" is 9.65°, theoretically no light should escape from the cell when methanol is the solvent (if light scattering is ignored). Since water or methanol are the lowest refractive index solvents most frequently used, a measurement instrument in accordance with the present invention has broad utility and no light will escape from the cell when other, higher refractive solvents are used.

While a preferred embodiment has been shown and described, various modifications and substitutions may be made thereto without departing from the spirit and scope of the invention. Accordingly, it is to be understood that the present invention has been described by way of illustration and not limitation.

What is claimed is:

1. A method of detecting the presence of an analyte in a solvent stream, said method comprising the steps of:
    fabricating a waveguide capillary from a fluorocarbon polymer having a refractive index of less than 1.33, the capillary having spatially displaced inlet and discharge ports;
    delivering the solvent containing the dissolved analyte to the inlet port of the waveguide;
    maintaining a pressure differential between the waveguide inlet and discharge ports whereby a solvent stream will flow through the waveguide and will form the light transmitting core thereof;
    inserting the first end of a first optical fiber into the waveguide core at a point displaced from the flow path between the inlet and discharge ports, the optical fiber being in intimate contact with the solvent;
    coupling a source of measurement light to the second end of the first optical fiber whereby light will be launched into the solvent stream flowing between the waveguide inlet and discharge ports; and
    receiving and analyzing light resulting from the passage of light from the source through the waveguide.

2. The method of claim 1 wherein the attenuation of light resulting from absorbance by the analyte is to be determined, the waveguide defined flow path is linear along at least a part of its length and the measurement light is launched into the solvent stream along the axis of said linear flow path.

3. The method of claim 2 wherein the first end of the first optical fiber is located adjacent to and in registration with a first end of the linear flow path and the step of receiving and analyzing includes:
    positioning the first end of a second optical fiber adjacent to and in registration with the second end of the linear flow path to collect light which has passed through the waveguide liquid core.

4. The method of claim 2 wherein the first end of the first optical fiber is located adjacent to and in registration with a first end of the linear flow path and the step of receiving and analyzing includes:
    positioning a mirror in registration with and adjacent to the second end of the linear flow path to cause light coupled to the wave guide core to be reflected and twice traverse the length of the linear flow path;
    collecting the reflected light received at the first end of the linear flow path with the first optical fiber; and
    separating the received reflected light from the light from the source and thereafter analyzing the separated light.

5. The method of claim 1 wherein the solvent is selected from the group consisting of aqueous solutions and methanol.

6. The method of claim 3 wherein the solvent is selected from the group consisting of aqueous solutions and methanol.

7. The method of claim 4 wherein the solvent is selected from the group consisting of aqueous solutions and methanol.

8. The method of claim 1 wherein the fluorescence resulting from the excitation of the analyte by the measurement light is to be measured and the step of receiving and analyzing includes juxtapositioning a light sensitive detector to the waveguide defined flow path along at least a portion thereof intermediate the inlet and discharge parts.

9. The method of claim 8 wherein the step of fabricating the wave guide includes causing at least a portion of the core region thereof to have an axis which lies in a plane and wherein the step of juxtapositioning the light sensitive detector comprises locating the detector so that it is symmetrical with respect to a plane which is substantially parallel to the plane of the waveguide core region.

10. The method of claim 8 wherein the step of receiving and analyzing further comprises:
   positioning a reflector on the opposite side of the waveguide with respect to the detector.

11. The method of claim 9 wherein the waveguide core defines a non-linear flow path between the inlet and discharge ports.

12. The method of claim 11 wherein the step of receiving and analyzing further comprises:
   positioning a reflector on the opposite side of the waveguide with respect to the detector.

13. The method of claim 1 wherein the measurement light is either ultraviolet or in the visible spectrum.

14. The method of claim 1 wherein the solvent is the effluent from chromatography or electrophoresis.

15. A flow-through cell for use in the measurement of chemical properties of small volumes of fluid containing dissolved analytes, said cell comprising:
   a rigid capillary tube, said tube having a core region which defines a flow path, said flow path having an axis, said tube having a wall which interfaces with said core region, said wall having an index of refraction which is less than 1.32;
   means defining an inlet port for delivery of a fluid to be analyzed to said core region, said inlet port providing fluid communication with said core region;
   means defining a discharge port in fluid communication with said core region, said discharge port being displaced from said inlet port along said flow path, fluid delivered to said core region through said inlet port flowing along said flow path and exiting said core region through said discharge port;
   means for transmitting light energy into said core region whereby the fluid to be analyzed will function as the light conducting medium of a liquid core waveguide, the guided light being generally coaxial with said flow path; and
   light receiving means.

16. The flow-through cell of claim 15 wherein said capillary tube is comprised of a fluorocarbon polymer.

17. The flow-through cell of claim 15 wherein said flow path is at least in part linear between said inlet and discharge ports and said light transmitting means comprises a first optical fiber which directly communicates with said core region at a first end of said linear flow path port.

18. The flow-through cell of claim 17 wherein said light receiving means comprises a second optical fiber which directly communicates with said core region at the second end of said linear flow path port.

19. The flow-through cell of claim 17 further comprising:
   a mirror positioned adjacent to the second end of said linear flow path port, said mirror reflecting light back along said flow path to said light energy transmitting means; and
whereas said light receiving means comprises:
   said first optical fiber; and
   means for separating reflected light received at said first optical fiber from measurement light delivered to said first optical fiber.

20. The flow-through cell of claim 15 wherein said light receiving means comprises:
   a light sensitive detector positioned along at least a portion of said flow path on a first side thereof and external of said tube.

21. The flow-through cell of claim 20 wherein said light receiving means further comprises:
   reflector means positioned on the opposite side of said tube with respect to said detector, said reflector means being shaped and located to reflect light passing through the tube wall to said detector.

* * * * *